United States Patent
Yoda et al.

(10) Patent No.: US 12,320,768 B2
(45) Date of Patent: Jun. 3, 2025

(54) MEASURING DEVICE AND MEASURING SYSTEM

(71) Applicant: SHINKO ELECTRIC INDUSTRIES CO., LTD., Nagano (JP)

(72) Inventors: Atsuto Yoda, Nagano (JP); Takuya Horiuchi, Nagano (JP)

(73) Assignee: SHINKO ELECTRIC INDUSTRIES CO., LTD., Nagano (JP)

( * ) Notice: Subject to any disclaimer, the term of this patent is extended or adjusted under 35 U.S.C. 154(b) by 363 days.

(21) Appl. No.: 18/154,366

(22) Filed: Jan. 13, 2023

(65) Prior Publication Data
US 2023/0243772 A1  Aug. 3, 2023

(30) Foreign Application Priority Data
Feb. 3, 2022  (JP) .................. 2022-015632

(51) Int. Cl.
*G01N 27/22* (2006.01)
*G01N 33/18* (2006.01)

(52) U.S. Cl.
CPC ......... *G01N 27/226* (2013.01); *G01N 27/221* (2013.01); *G01N 33/18* (2013.01)

(58) Field of Classification Search
CPC ...... G01N 27/226; G01N 27/221; G01N 33/18
USPC ....................................... 73/53.01
See application file for complete search history.

(56) References Cited

U.S. PATENT DOCUMENTS

| | | | |
|---|---|---|---|
| 2006/0073077 A1* | 4/2006 | Centanni | G01N 33/0032 436/155 |
| 2019/0038455 A1* | 2/2019 | Heitz | A61B 5/6833 |
| 2023/0003678 A1* | 1/2023 | Matoba | G01N 33/48735 |

FOREIGN PATENT DOCUMENTS

JP   H05-099872   4/1993

* cited by examiner

*Primary Examiner* — Peter J Macchiarolo
*Assistant Examiner* — John M Royston
(74) *Attorney, Agent, or Firm* — IPUSA, PLLC

(57) ABSTRACT

A measuring device includes a substrate having a first surface and a second surface on an opposite side from the first surface, a first electrode and a second electrode provided on the substrate, a heat-sensitive portion, provided on the first surface, and configured to detect heat of a substance that makes contact with the first surface, a temperature sensor provided on the second surface, and a heat transfer member, penetrating the substrate, and configured to transfer heat of the heat-sensitive portion to the temperature sensor.

13 Claims, 17 Drawing Sheets

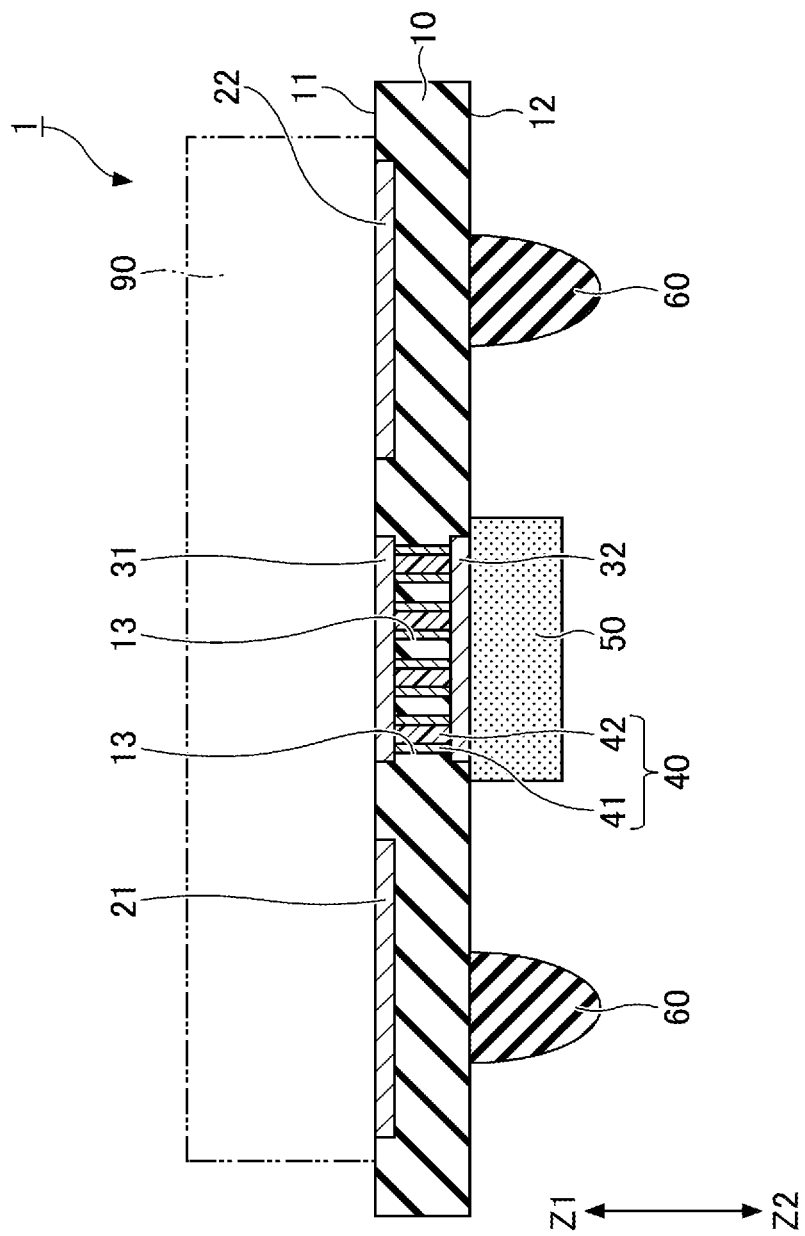

MEASURING DEVICE AND MEASURING SYSTEM

CROSS-REFERENCE TO RELATED APPLICATIONS

This application is based upon and claims priority to Japanese Patent Application No. 2022-015632, filed on Feb. 3, 2022, the entire contents of which are incorporated herein by reference.

FIELD

Certain aspects of the embodiments discussed herein are related to measuring devices and measuring systems.

BACKGROUND

As a method for measuring a solute concentration in a solution, there is a method that inserts electrodes into the solution and measures a resistance or the like between the electrodes.

An example of an electrochemical measuring method is proposed in Japanese Laid-Open Patent Publication No. H05-99872, for example.

However, in the conventional measuring method, a satisfactory measurement accuracy may not be obtained due corrosion or the like of the electrodes. In addition, in a case where physical properties to be measured are temperature dependent, it is difficult to obtain satisfactory measurement accuracy unless the temperature of the solution is adjusted.

SUMMARY

Accordingly, it is an object in one aspect of the embodiments to provide a measuring device and a measuring system capable of performing a measurement with a satisfactory measurement accuracy even in the case where physical properties to be measured are temperature dependent.

According to one aspect of the embodiments, a measuring device includes a substrate having a first surface and a second surface on an opposite side from the first surface; a first electrode and a second electrode provided on the substrate; a heat-sensitive portion, provided on the first surface, and configured to detect heat of a substance that makes contact with the first surface; a temperature sensor provided on the second surface; and a heat transfer member, penetrating the substrate, and configured to transfer heat of the heat-sensitive portion to the temperature sensor.

The object and advantages of the embodiments will be realized and attained by means of the elements and combinations particularly pointed out in the claims.

It is to be understood that both the foregoing general description and the following detailed description are exemplary and explanatory and not restrictive of the invention, as claimed.

BRIEF DESCRIPTION OF DRAWINGS

FIG. 2 is a cross sectional view illustrating the measuring device according to the first embodiment;

DESCRIPTION OF EMBODIMENTS

Figure 1A:
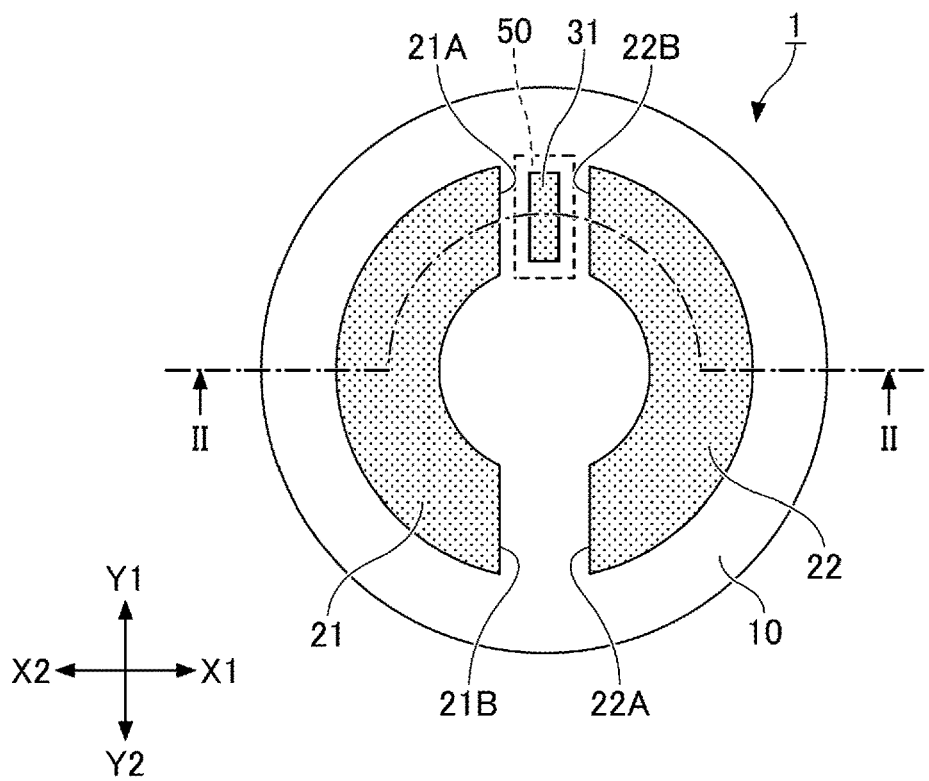
FIG. 1A and FIG. 1B are diagrams illustrating a measuring device according to a first embodiment.

Preferred embodiments of the present invention will be described with reference to the accompanying drawings. In the drawings, those constituent elements having substantially the same functional configuration are designated by the same reference numerals, and a repeated description of the same constituent elements may be omitted. In the present disclosure, an X1-X2 direction, a Y1-Y2 direction, and a Z1-Z2 direction are mutually perpendicular directions. A plane including the X1-X2 direction and the Y1-Y2 direction will be referred to as an XY-plane, a plane including the Y1-Y2 direction and the Z1-Z2 direction will be referred to as a YZ-plane, and a plane including the Z1-Z2 direction and the X1-X2 direction will be referred to as a ZX-plane. For the sake of convenience and simplicity, the Z1-Z2 direction may also be referred to as a vertical (or up-down) direction, the Z1-side may be referred to as an upper side, and the Z2-side may be referred to as a lower side. In addition, a plan view refers to a view of an object from the Z1-side, and a planar shape refers to a shape of the object in the plan view viewed from the Z1-side.

First Embodiment

Figure 1B:
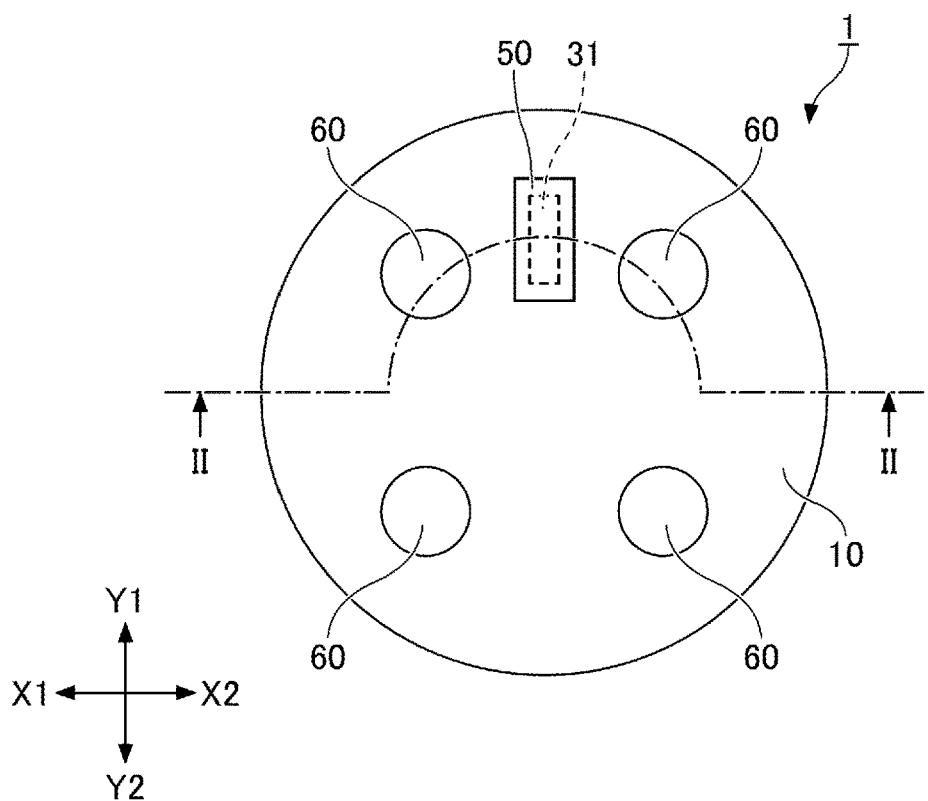

A first embodiment relates to a measuring device. FIG. 1A, FIG. 1B, and FIG. 2 are diagrams illustrating the measuring device according to the first embodiment. FIG. 1A is a top view of the measuring device, and FIG. 1B is a bottom view of the measuring device. FIG. 2 corresponds to a cross sectional view along a line II-II in FIG. 1A and FIG. 1B.

As illustrated in FIG. 1A, FIG. 1B, and FIG. 2, a measuring device 1 according to the first embodiment includes a substrate 10, a first electrode 21, a second electrode 22, a first copper (Cu) film 31, a second copper (Cu) film 32, heat transfer vias 40, a temperature sensor 50, and a plurality of spacers 60.

The substrate 10 has a first surface 11, and a second surface 12 on an opposite side from the first surface 11. The first surface 11 is a surface on the Z1-side, that is, an upper surface. The second surface 12 is a surface on the Z2-side, that is, a lower surface. The substrate 10 has a planar shape that is circular, for example. The substrate 10 is an insulating substrate. A material used for the substrate 10 is a glass epoxy or the like, for example. A thickness of the substrate 10 is in a range of approximately 600 μm to approximately 1500 μm, for example.

As illustrated in FIG. 2, the measuring device 1 is used in a state where a measuring object 90, that is a target to be measured, is placed on the first surface 11. The measuring object 90 has physical properties that are temperature dependent. Examples of such physical properties include a dielectric constant and a conductivity. The measuring object 90 includes a glass container, and a substance, such as water or the like, sealed inside the glass container.

The first electrode 21 and the second electrode 22 are provided on the first surface 11, for example. The first electrode 21 and the second electrode 22 are electrically insulated from each other. Each of the first electrode 21 and the second electrode 22 has a planar shape that is approximately arcuate band-shaped, for example. The first electrode 21 has one end portion 21A and the other end portion 21B, and the second electrode 22 has one end portion 22A and the other end portion 22B. The one end 21A of the first electrode 21 and the other end 22B of the second electrode 22 oppose each other, and the other end 21B of the first electrodes 21 and the one end 22A of the second electrode 22 oppose each other. The first electrode 21 and the second electrode 22 are curved so as to separate from each other. Each of the first electrode 21 and the second electrode 22 includes a copper film or the like, for example. Thicknesses of the first electrode 21 and the second electrode 22 are in a range of approximately 12 μm to approximately 30 μm, for example.

The first copper film 31 is provided on the first surface 11. The first copper film 31 is provided between the one end 21A of the first electrode 21 and the other end 22B of the second electrode 22. The first copper film 31 has a planar shape that is rectangular, for example. A thickness of the first copper film 31 is in a range of approximately 12 μm to approximately 30 μm, for example. The first copper film 31 is an example of a heat-sensitive portion.

The second copper film 32 is provided on the second surface 12. The second copper film 32 has a planar shape that is rectangular, for example. The second copper film 32 overlaps the first copper film 31 in the plan view viewed in a direction perpendicular to the first surface 11. A thickness of the second copper film 32 is in a range of approximately 12 μm to approximately 30 μm, for example.

A plurality of via holes 13 is formed in the substrate 10. In the plan view viewed in the direction perpendicular to the first surface 11, the plurality of via holes 13 is formed on an inner side of a contour of the first copper film 31 and a contour of the second copper film 32. The plurality of via holes 13 extends in a direction (Z1-Z2 direction) perpendicular to the first surface 11, and reaches the first copper film 31 and the second copper film 32. A diameter of each via hole 13 is in a range of approximately 150 μm to approximately 300 μm, for example.

The heat transfer vias 40 are provided in the plurality of via holes 13, respectively, and make direct contact with the first copper film 31 and the second copper film 32. The heat transfer vias 40 extend in the direction (Z1-Z2 direction) perpendicular to first surface 11. Each heat transfer via 40 includes a third copper film 41 covering an inner wall surface of the via hole 13, and a filler material 42 filling an inner side of the third copper film 41, for example. The third copper film 41 makes direct contact with the first copper film 31 and the second copper film 32. The filler material 42 is a resin, for example. A thickness of the third copper film 41 is in a range of approximately 12 μm to approximately 20 μm, for example. The second copper film 32, the heat transfer vias 40, and the third copper film 41 are examples of a heat transfer member.

The temperature sensor 50 is provided on the second surface 12. The temperature sensor 50 makes contact with the second copper film 32. In the plan view viewed in the direction perpendicular to the first surface 11, the first copper film 31 and the temperature sensor 50 overlap each other, for example. The temperature sensor 50 measures a temperature of the second copper film 32. The temperature sensor 50 includes a thermocouple, for example, and measures a temperature of the measuring object 90 placed on the first surface 11, through the second copper film 32, the heat transfer vias 40, and the first copper film 31.

The plurality of spacers 60 is provided on the second surface 12. Three or more spacers 60, and four spacers 60 in this example, are provided. The plurality of spacers 60 is provided around the temperature sensor 50. A height (or thickness) of each spacer 60 is greater than the thickness of the temperature sensor 50.

As described above, the measuring device 1 is used in the state where the measuring object 90 is placed on the first surface 11, as illustrated in FIG. 2. The measuring object 90 is placed (or set) on the first surface 11, so as to make contact with the first copper film 31, and the measuring device 1 is capable of measuring desired physical properties of the measuring object 90 using the first electrode 21 and the second electrode 22.

According to the first embodiment, it is possible to simultaneously measure the physical properties and the temperature of the measuring object 90, using the first electrode 21 and the second electrode 22. For this reason, even in the case where the physical properties are temperature dependent, it is possible to measure the physical properties according to the temperature with a high accuracy.

For example, in the case where the measuring object 90 includes the glass container, and the water sealed inside the glass container, it is possible to measure a concentration of carbonate (calcium carbonate, magnesium carbonate, or the like) included in the water. In this state, a dielectric constant between the first electrode 21 and the second electrode 22 varies according to the concentration of the carbonate. Hence, by measuring the dielectric constant between the first electrode 21 and the second electrode 22, it is possible to perform a contactless measurement of the concentration of carbonate. Accordingly, it is possible to reduce a deterioration in the accuracy caused by corrosion or the like of the first electrode 21 and the second electrode 22. In addition, although the concentration of carbonate in the water is temperature dependent, the concentration of carbonate can be measured with a high accuracy, because a temperature of the water can be measured by the temperature sensor 50. Moreover, because the heat transfer vias 40 penetrating the substrate 10 transfer heat of the first copper film 31 to the temperature sensor 50, heat of the measuring object 90 is transferred to the temperature sensor 50 with a low loss.

Figure 3:
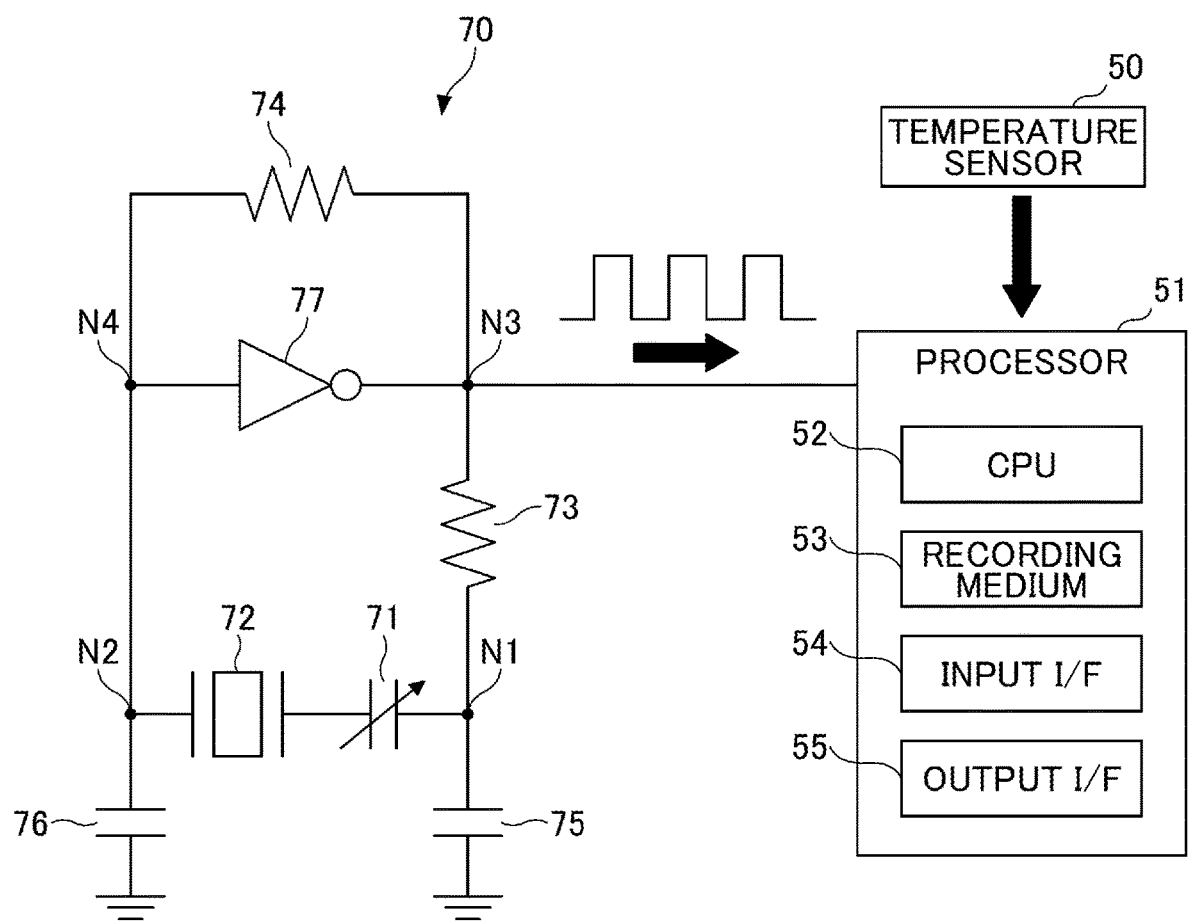
FIG. 3 is a circuit diagram illustrating an example of a detection circuit.

Next, an example of a detection circuit, to which the first electrode 21 and the second electrode 22 are connected, will be described. This detection circuit is used to detect the dielectric constant between the first electrode 21 and the second electrode 22. FIG. 3 is a circuit diagram illustrating an example of the detection circuit.

As illustrated in FIG. 3, a detection circuit 70, to which the first electrode 21 and the second electrode 22 are connected, includes a variable capacitor 71, a crystal oscillator (Xtal) 72, a resistance element 73, a resistance element 74, a capacitor 75, a capacitor 76, and an inverter 77. The detection circuit 70 further includes nodes N1, N2, N3, and N4. The variable capacitor 71 includes the first electrode 21 and the second electrode 22, and a capacitance of the variable capacitor 71 varies according to the dielectric constant between the first electrode 21 and the second electrode 22.

The variable capacitor 71 and the crystal oscillator 72 are connected in series between the node N1 and the node N2. One end of the capacitor 75 is connected to the node N1, and the other end of the capacitor 75 is grounded. One end of the capacitor 76 is connected to the node N2, and the other end of the capacitor 76 is grounded. The resistance element 73 is connected between the node N1 and the node N3. The node N2 and the N4 are short-circuited, and the resistance element 74 and the invertor 77 are connected in parallel between the node N3 and the node N4. An input of the invertor 77 is connected to the node N4, and an output of the inverter 77 is connected to the node N3.

In the detection circuit 70, a capacitance of the variable capacitor 71 varies according to the dielectric constant between the first electrode 21 and the second electrode 22, and a frequency of an AC signal output from the node N3 varies according to the capacitance of the variable capacitor 71. Accordingly, the dielectric constant between the first electrode 21 and the second electrode 22 can be determined, by analyzing the frequency of the AC signal. In the case where the measuring object 90 includes the glass container, and the water sealed inside the glass container as described above, the concentration of carbonate in the water can be determined from the dielectric constant between the first electrode 21 and the second electrode 22. The AC signal output from the node N3 is sometimes also referred to as a clock signal.

As illustrated in FIG. 3, a measuring system suitable for measuring the concentration of carbonate in the water includes the detection circuit 70, and a processor 51.

The processor 51 is a computer, for example, and includes a central processing unit (CPU) 52, a recording medium 53, such as a memory or the like, an input interface (I/F) 54, and an output interface (I/F) 55. The recording medium 53 stores one or more programs for controlling various processes executed in the measuring system. The processor 51 receives a signal from an outside through the input I/F 54, and transmits a signal to the outside through the output I/F 55. The processor 51 receives an output signal of the temperature sensor 50, and an output signal (AC signal) of the detection circuit 70, and the CPU 52 executes the one or more programs stored in the recording medium 53. Accordingly, the measuring system measures the concentration of carbonate in the water included in the measuring object 90.

The one or more programs may be stored in a computer-readable recording medium, and installed from the computer-readable recording medium to the recording medium 53 of the processor 51. Examples of the computer-readable recording medium include a hard disk (HD), a flexible disk (FD), a compact disk (CD), a magneto-optical (MO) disk, a memory card, or the like, for example. The one or more programs may be downloaded from a server (not illustrated) via the Internet, and installed in the recording medium 53 of the processor 51. Each of the computer-readable recording medium and the recording medium 53 may be a non-transitory recording medium, for example.

Figure 4:
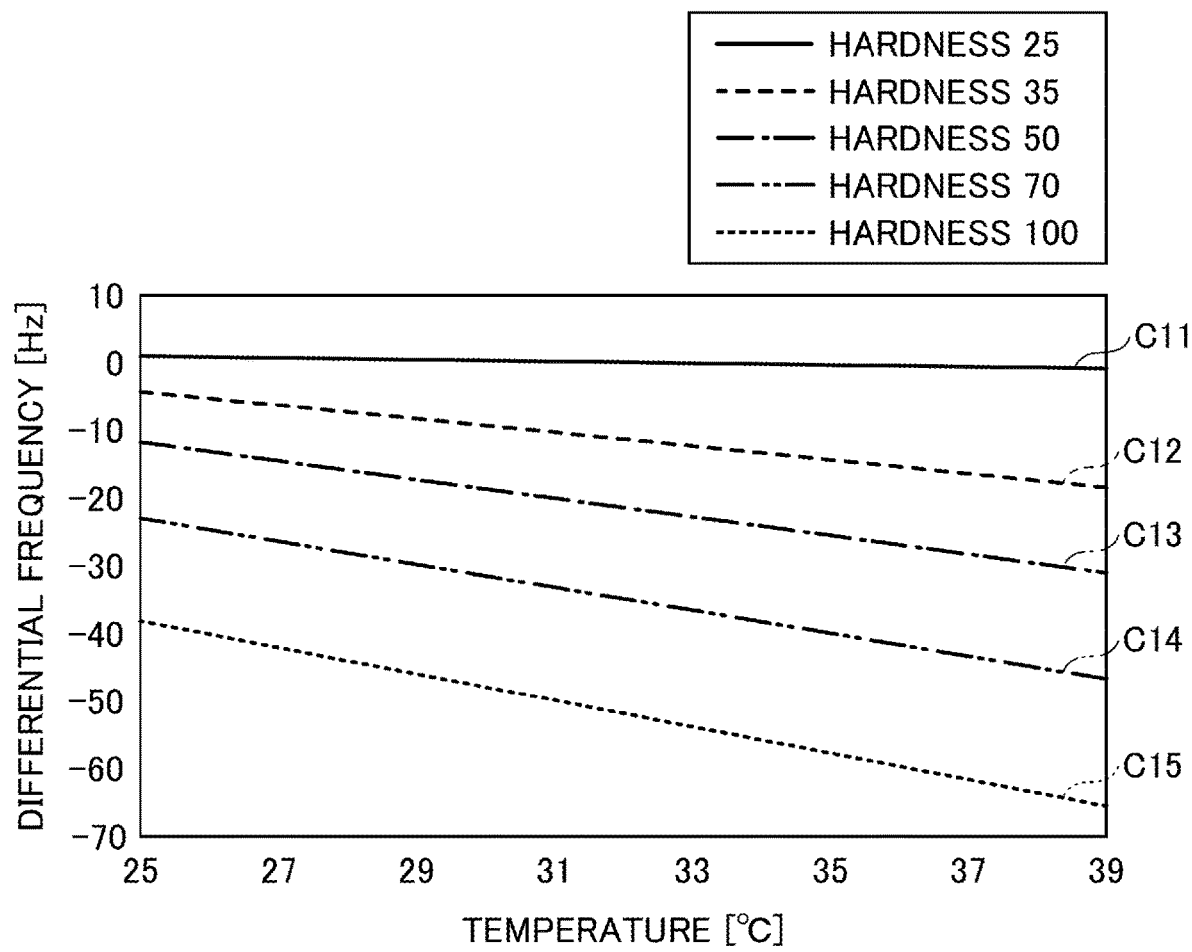
FIG. 4 is a diagram illustrating examples of data of calibration curves.

In addition to the one or more programs described above, reference data created using data of calibration curves acquired in advance are also stored in the recording medium 53. FIG. 4 is a diagram illustrating examples of the data of the calibration curves. In FIG. 4, the abscissa indicates the temperature, and the ordinate indicates the differential frequency. The data illustrated in FIG. 4 are data acquired using water having a known hardness. A hardness X indicates that the concentration of carbonate is X [mg/l]. In this case, the differential frequency is a difference of the frequency of the AC signal output from the node N3 from a reference frequency, and the reference frequency is the frequency of the AC signal output from the node N3 when the measurement is performed on the water having a hardness of 25 and a temperature of 25° C. Accordingly, measuring the differential frequency corresponds to measuring the dielectric constant between the first electrode 21 and the second electrode 22.

As illustrated in FIG. 4, a slope of a calibration curve C11 for the hardness of 25 is −0.1 Hz/° C., the slope of a calibration curve C12 for the hardness of 35 is −1.0 Hz/° C., the slope of a calibration curve C13 for the hardness of 50 is −1.4 Hz/° C., the slope of a calibration curve C14 for the hardness of 70 is −1.7 Hz/° C., and the slope of a calibration curve C15 for the hardness of 100 is −2.0 Hz/° C.

Figure 5:
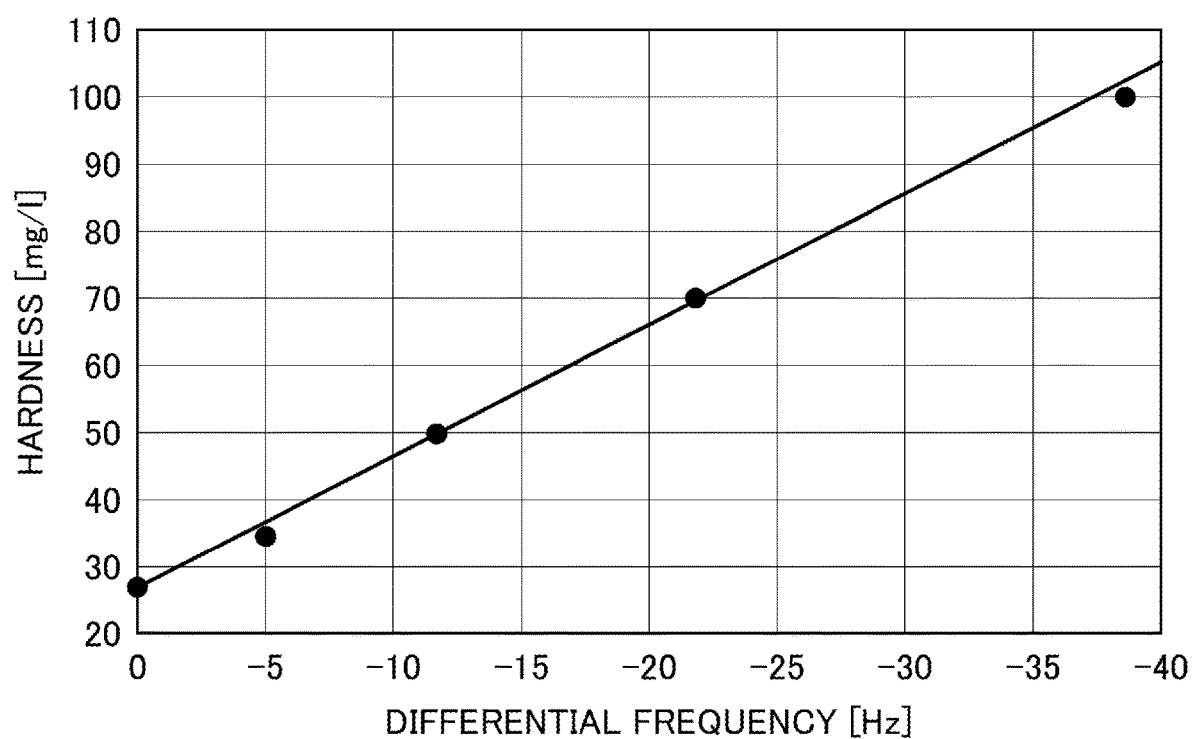
FIG. 5 is a diagram illustrating a relationship between a differential frequency and hardness.

FIG. 5 is a diagram illustrating a relationship between the differential frequency and the hardness. FIG. 5 illustrates the relationship between the differential frequency and the hardness at a temperature of 25° C. This relationship is acquired from the values of the differential frequency for each hardness when the temperature is 25° C. in FIG. 4.

Figure 6:
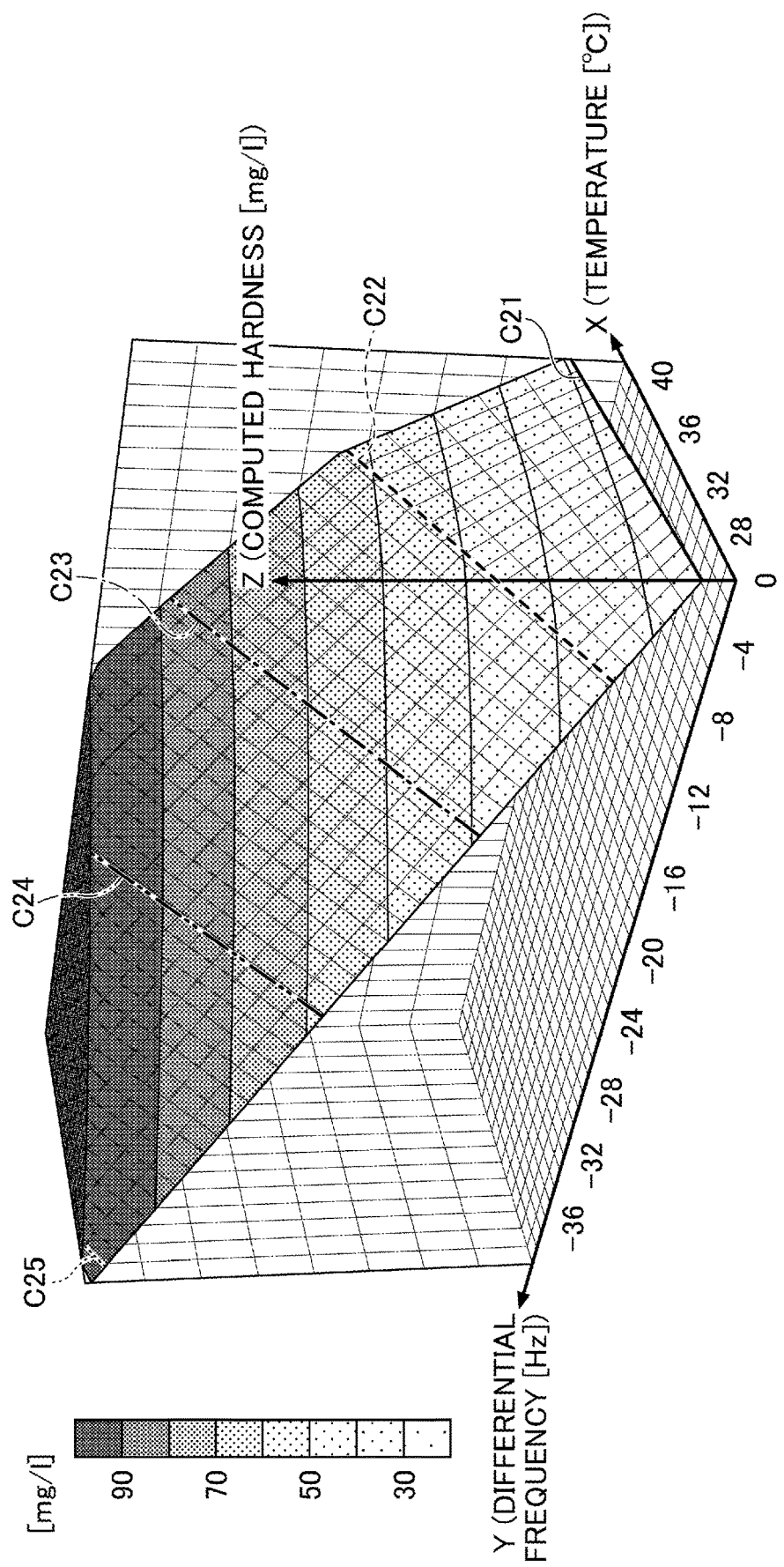
FIG. 6 is a diagram illustrating an example of reference data.

FIG. 6 is a diagram illustrating an example of the reference data. The reference data illustrated in FIG. 6 is created using the data of the calibration curves illustrated in FIG. 4, and the relationship illustrated in FIG. 5. The reference data is three-dimensional data represented using an XYZ coordinate system. The X-axis indicates the temperature, the Y-axis indicates the differential frequency, and the Z-axis indicates a computed hardness. This XYZ coordinate system used in FIG. 5 is unrelated to X1, X2, Y1, Y2, Z1, and Z2 in FIG. 1 or the like. The reference data illustrated in FIG. 5 are stored in the recording medium 53.

The reference data illustrated FIG. 6 can be created as follows. For example, a point A on an arbitrary calibration curve illustrated in FIG. 4 is selected, and a temperature $T_A$ and a differential frequency $F_A$ at this point A are read. Next, a hardness corresponding to the differential frequency $F_A$ is read from FIG. 5, as a computed hardness $H_A$. Further, a point having coordinates ($T_A$, $F_A$, $H_A$) is plotted in FIG. 6. By performing this operation for each point on each calibration curve illustrated in FIG. 4, the reference data illustrated in FIG. 6 are created. The computed hardness refers to the hardness that is computed by such an operation. In addition, five acquired calibration curves C21, C22, C23, C24, and C25 illustrated in FIG. 6 are acquired by the computation from the calibration curves C11, C12, C13, C14, and C15 illustrated in FIG. 4, respectively.

Figure 7:
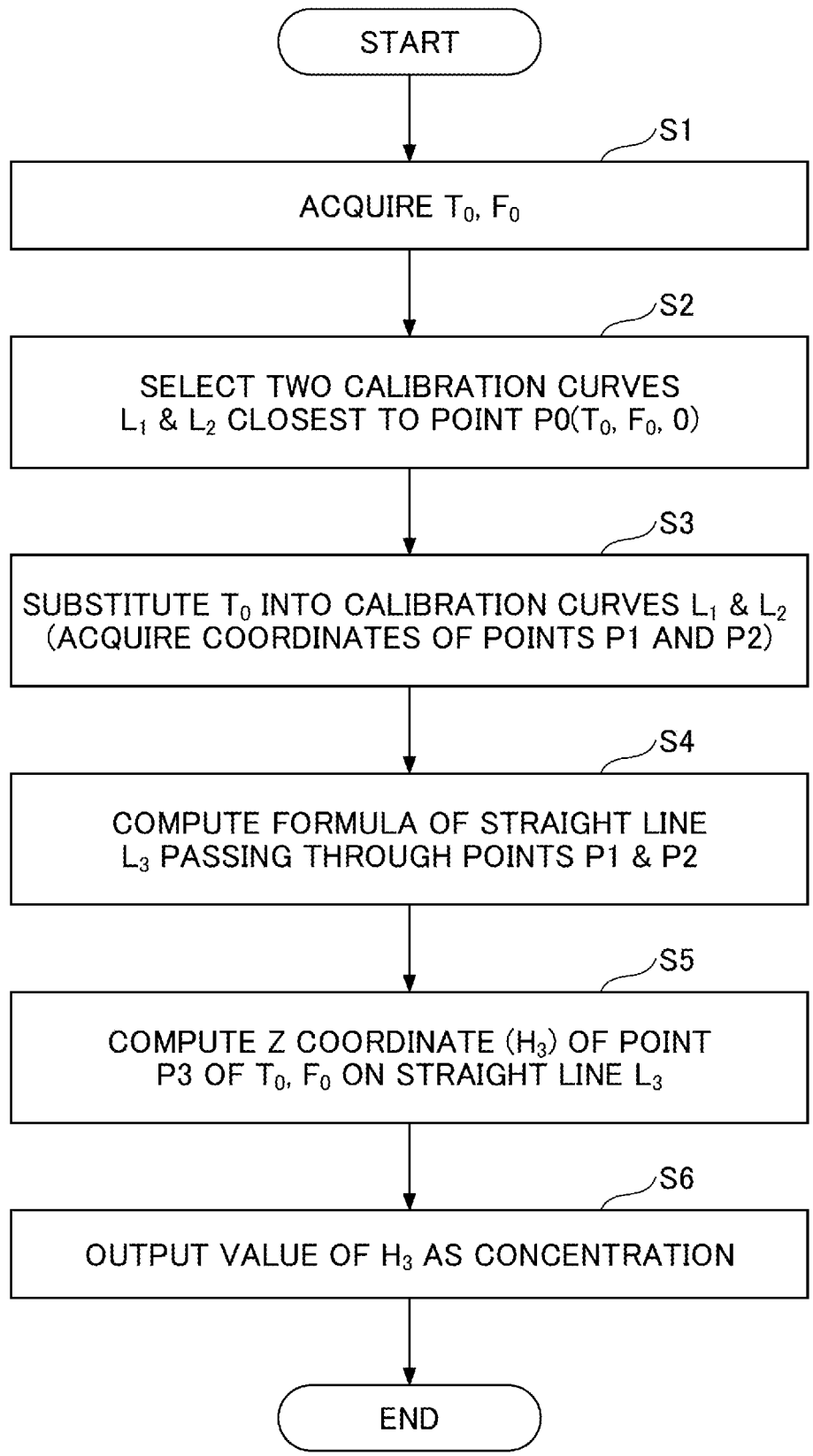
FIG. 7 is a flow chart illustrating an example of a program stored in a recording medium.

Next, an example of the programs stored in the recording medium 53 will be described. FIG. 7 is a flow chart illustrating an example of the program stored in the recording medium 53. FIG. 8 through FIG. 12 are diagrams illustrating a relationship between the program stored in the recording medium 53 and the reference data.

Figure 8:
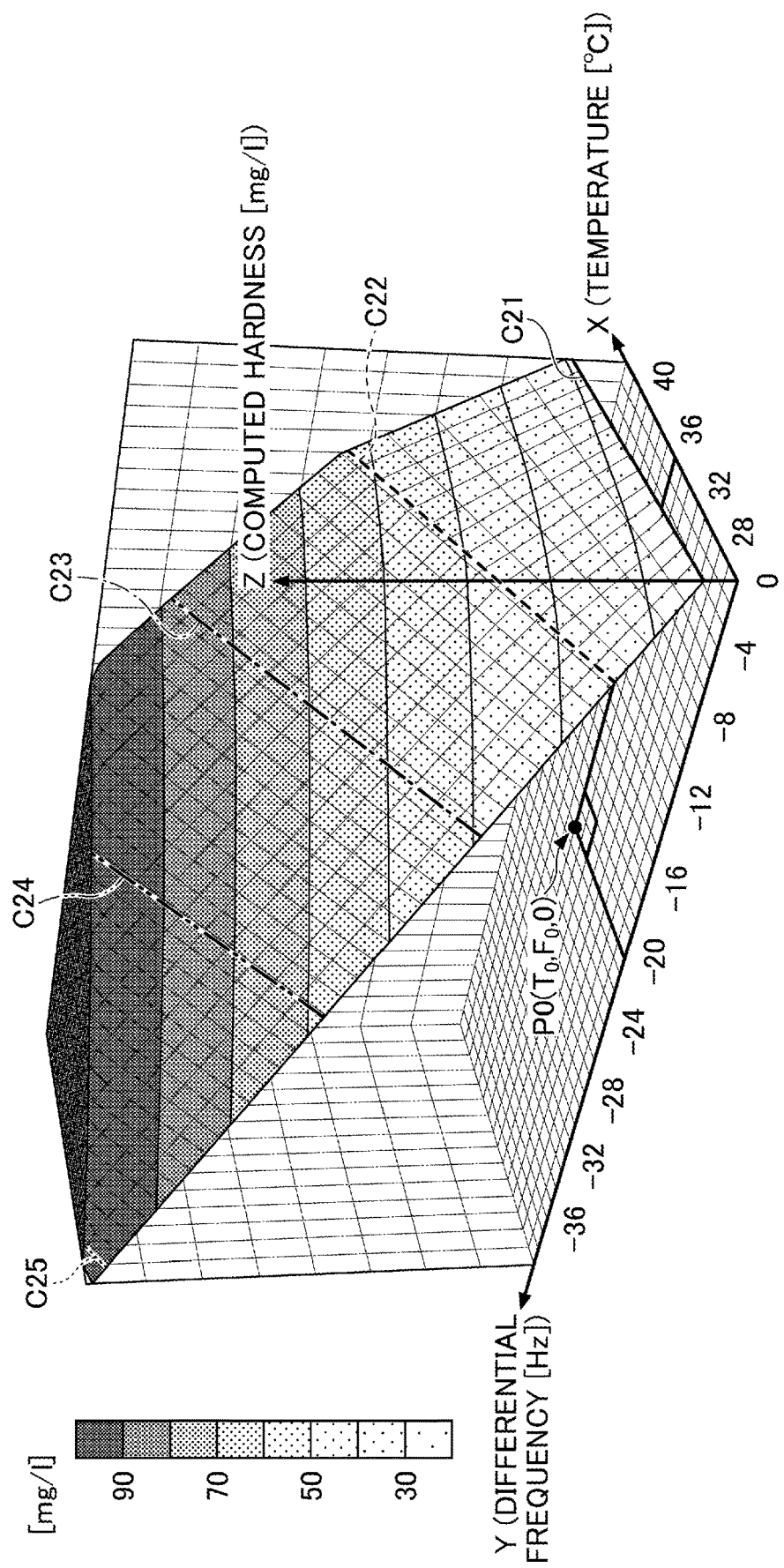
FIG. 8 is a diagram (part 1) illustrating a relationship between the program stored in the recording medium and the reference data.

First, the CPU 52 acquires the temperature $T_0$ of the measuring object 90 and the differential frequency $F_0$ of the AC signal output from the detection circuit 70 through the input interface 54 (step S1). FIG. 8 illustrates a point $P_0$ ($T_0$, $F_0$, 0) corresponding to the temperatures $T_0$ and the differential frequency $F_0$.

Figure 9:
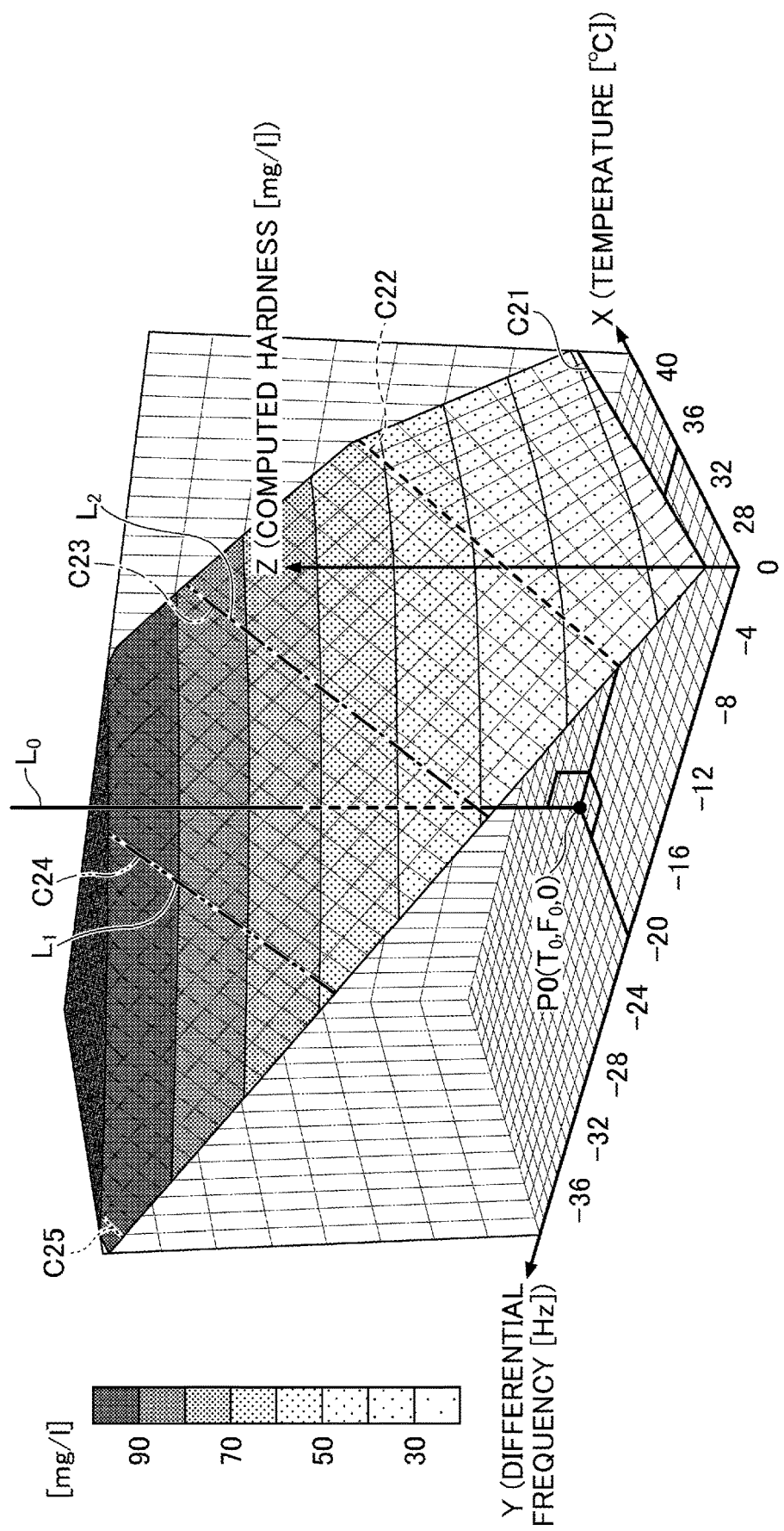
FIG. 9 is a diagram (part 2) illustrating the relationship between the program stored in the recording medium and the reference data.

Next, the CPU 52 extracts two acquired calibration curves $L_1$ and $L_2$ having a smallest distance from a straight line $L_0$ that passes through the point $P_0$ ($T_0$, $F_0$, 0) and is parallel to the Z-axis (step S2). FIG. 9 illustrates the straight line $L_0$ and the two acquired calibration curves $L_1$ and $L_2$. In this case, the acquired calibration curve C24 is one acquired calibration curve $L_1$, and the acquired calibration curve C23 is the other acquired calibration curve $L_2$.

Figure 10:
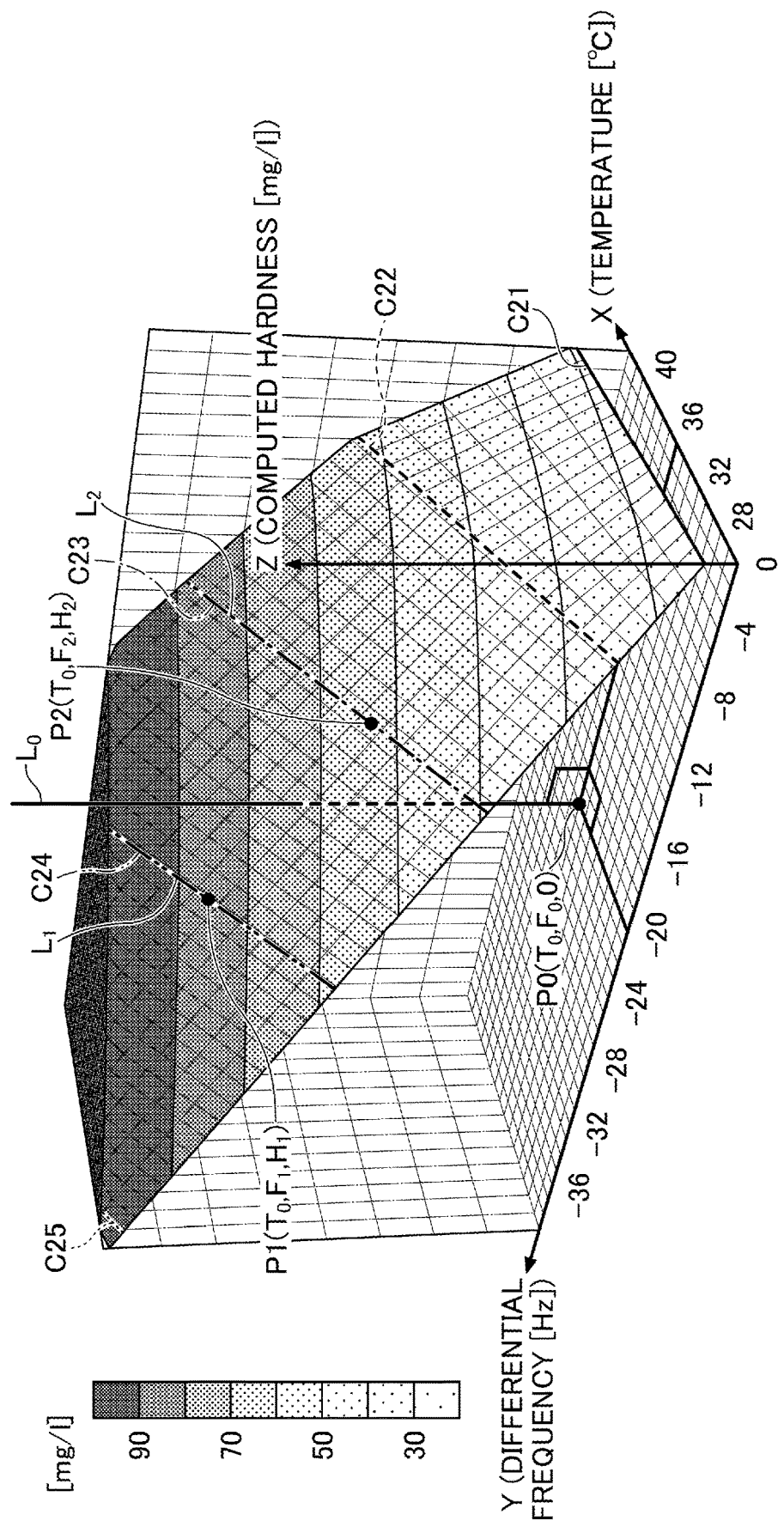
FIG. 10 is a diagram (part 3) illustrating the relationship between the program stored in the recording medium and the reference data.

Next, the CPU 52 inputs the temperature $T_0$ to the acquired calibration curve $L_1$, to acquire a differential frequency $F_1$ and a computed hardness $H_1$ corresponding to the temperature $T_0$, and inputs the temperature $T_0$ to the acquired calibration curve $L_2$, to acquire a differential frequency $F_2$ and a computed hardness $H_2$ corresponding to the temperature $T_0$ (step S3). As a result, coordinates of two points are acquired, as illustrated in FIG. 10. That is, coordinates ($T_0$, $F_1$, $H_1$) of a point $P_1$ on the acquired calibration curve $L_1$, and coordinates ($T_0$, $F_2$, $H_2$) of a point $P_2$ on the acquired calibration curve $L_2$, are acquired.

Figure 11:
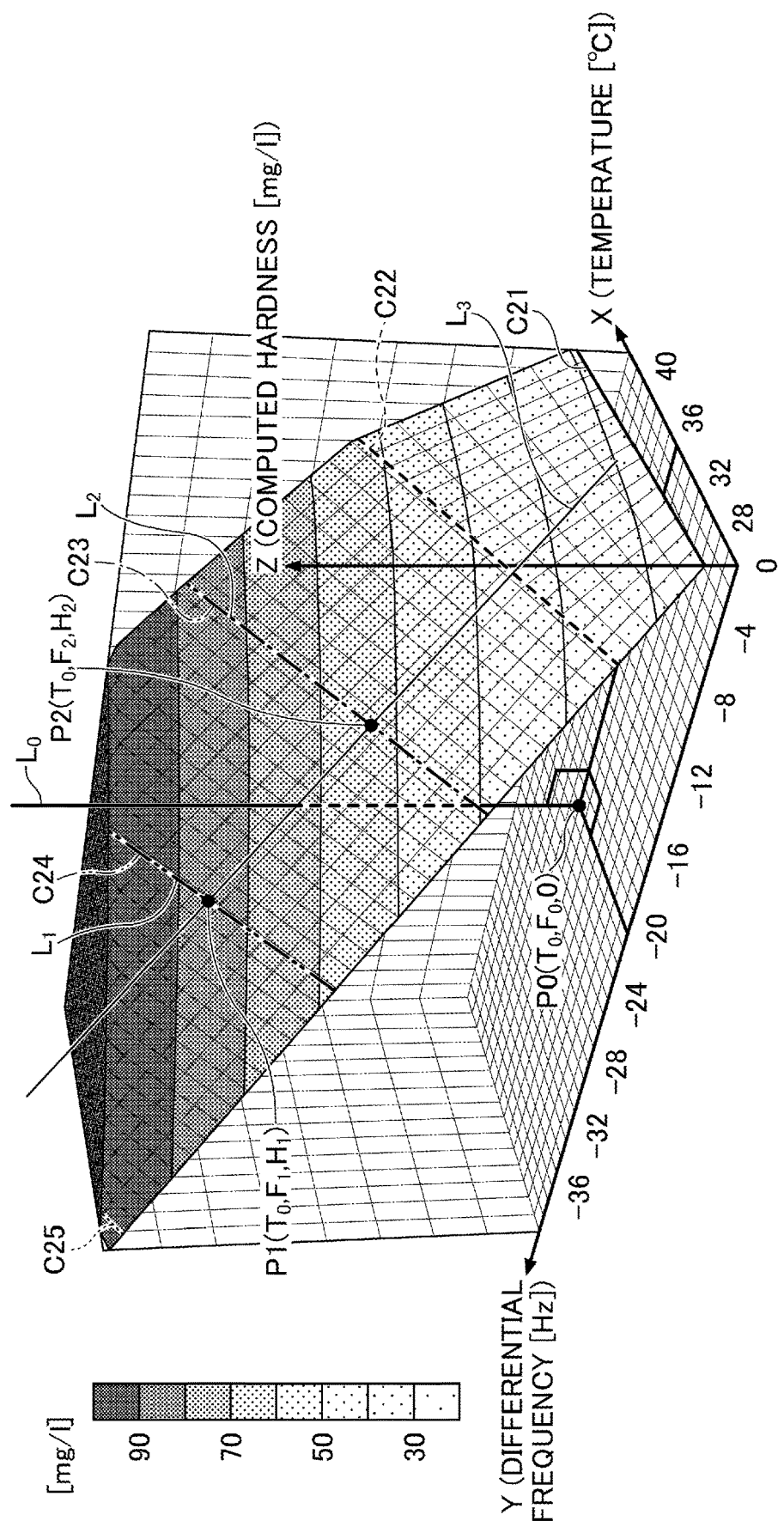
FIG. 11 is a diagram (part 4) illustrating the relationship between the program stored in the recording medium and the reference data.

Next, CPU 52 computes a formula of a straight line $L_3$ passing through the point $P_1$ and the point $P_2$ (step S4). FIG. 11 illustrates the straight line $L_3$. The formula of the straight line $L_3$ is expressed by the following.

$$Z = \frac{H_1 - H_2}{F_1 - F_2} Y + \frac{H_2 F_1 - H_1 F_2}{F_1 - F_2}$$

Figure 12:
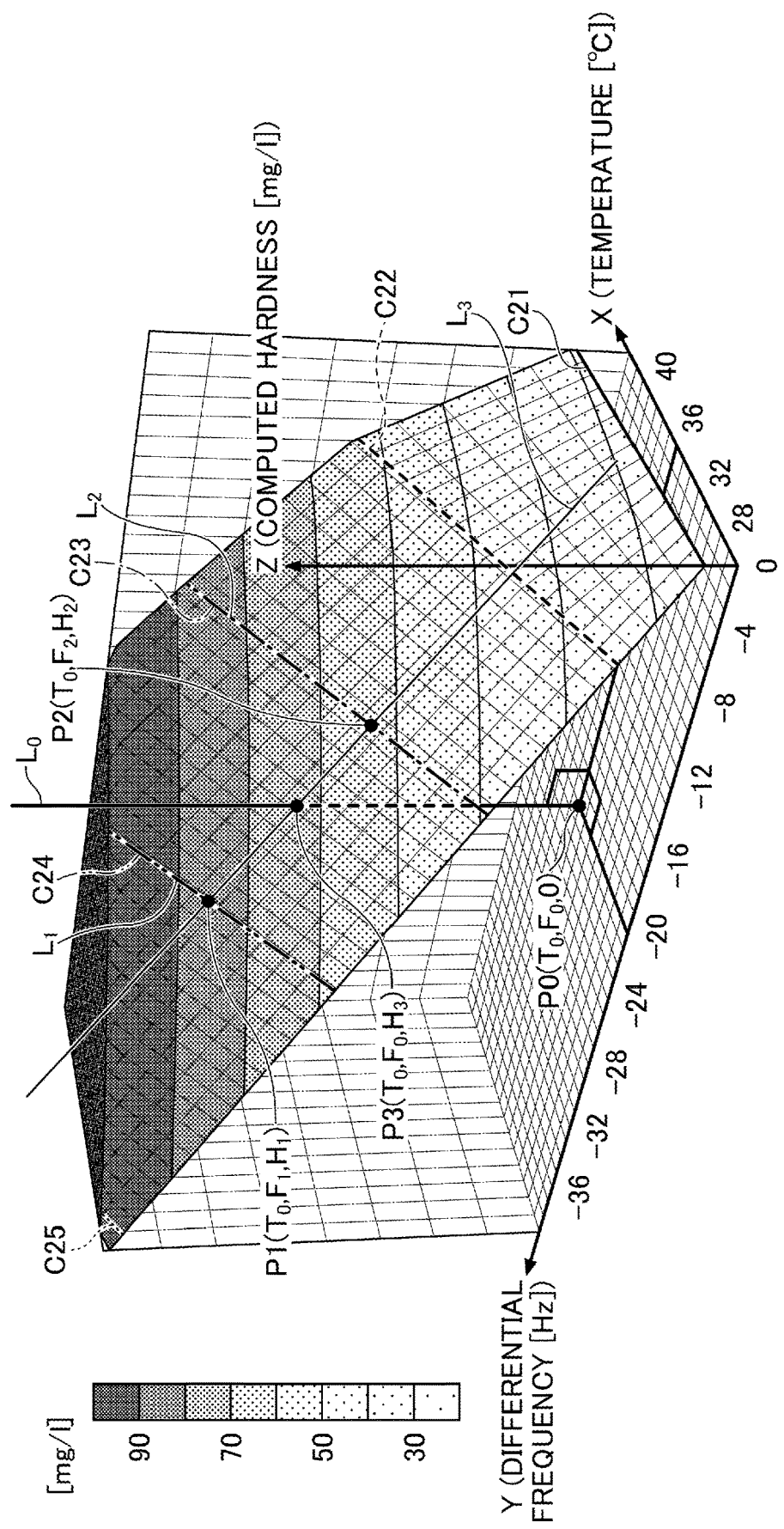
FIG. 12 is a diagram (part 5) illustrating the relationship between the program stored in the recording medium and the reference data.

Next, the CPU 52 computes coordinates ($T_0$, $F_0$, $H_3$) of an intersection point $P_3$ of the straight line $L_0$ and the straight line $L_3$ (step S5). More particularly, CPU 52 computes the Z-coordinate ($H_3$) of the intersection point $P_3$ as illustrated in FIG. 12, by substituting the differential frequency $F_0$ acquired in step S1 into Y of the straight line $L_3$.

Next, the CPU 52 outputs a value of the Z-coordinate ($H_3$) of the intersection point $P_3$, as the concentration of the carbonate in water, through the output I/F 55 (step S6).

The program stored in the recording medium 53 causes the processor 51 to perform such an operation described above.

According to the measuring system including the measuring device 1, the detection circuit 70, and the processor 51, it is possible to measure the concentration of the carbonate in water, that is temperature dependent, with a high accuracy by performing the processes based on the program stored in the recording medium 53.

Figure 13A:
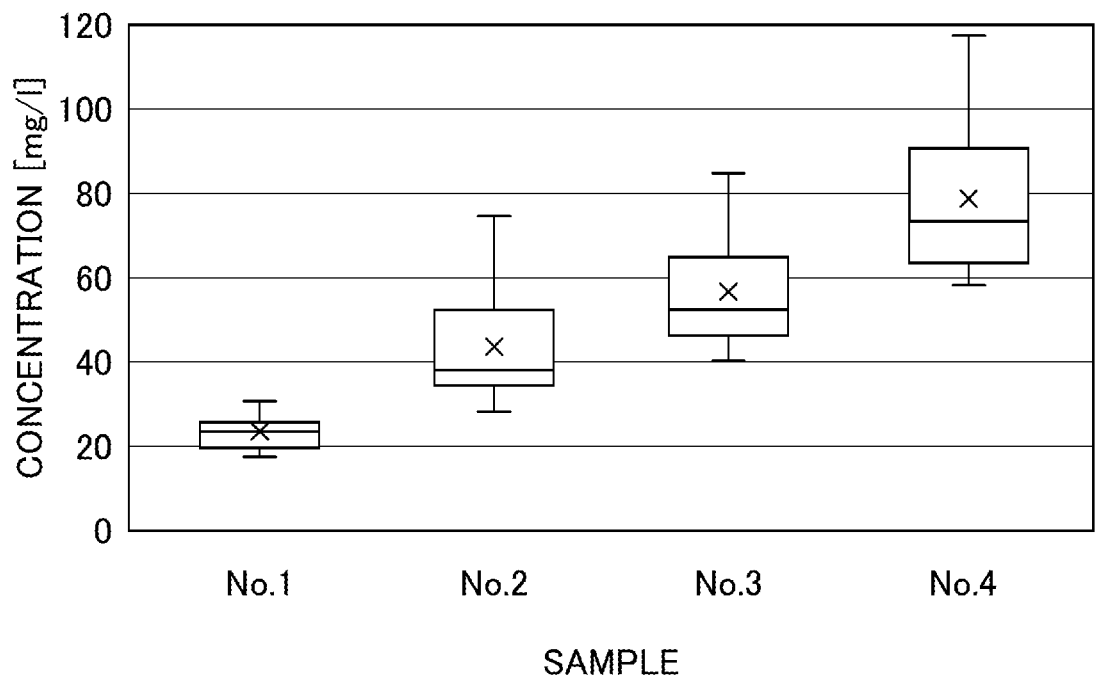
FIG. 13A and FIG. 13B are diagrams illustrating examples of measurement results of a concentration of carbonate.
Figure 13B:
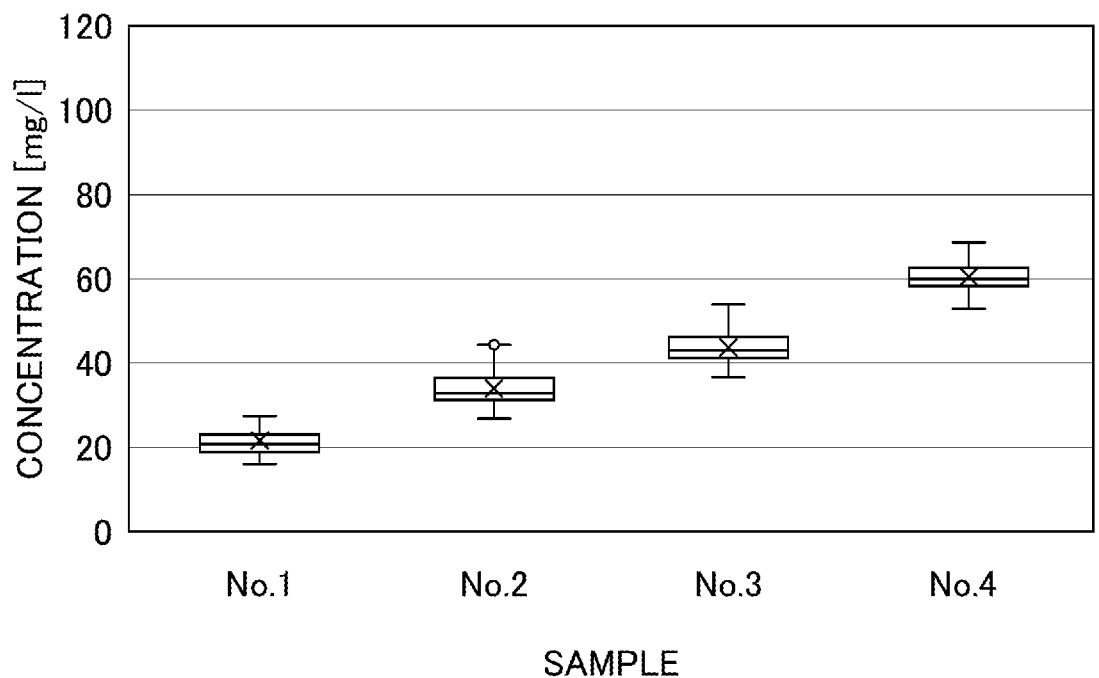

FIG. 13A and FIG. 13B are diagrams illustrating examples of measurement results of the concentration of carbonate. FIG. 13A illustrates the measurement result for a case using the calibration curve illustrating the relationship between the concentration and the differential frequency at the temperature of 25° C. FIG. 13B illustrates the measurement result for a case using the measuring system described above. Sample No. 1 in FIG. 13A and FIG. 13B is commercially available water having a hardness of 19, sample No. 2 is commercially available water having a hardness of 30, sample No. 3 is commercially available water having a hardness of 40, and sample No. 4 is commercially available water having a hardness of 59.

As illustrated in FIG. 13B, according to the measurement using the measuring system described above, it was possible to reduce inconsistencies and obtain an excellent measurement accuracy.

Second Embodiment

Figure 14A:
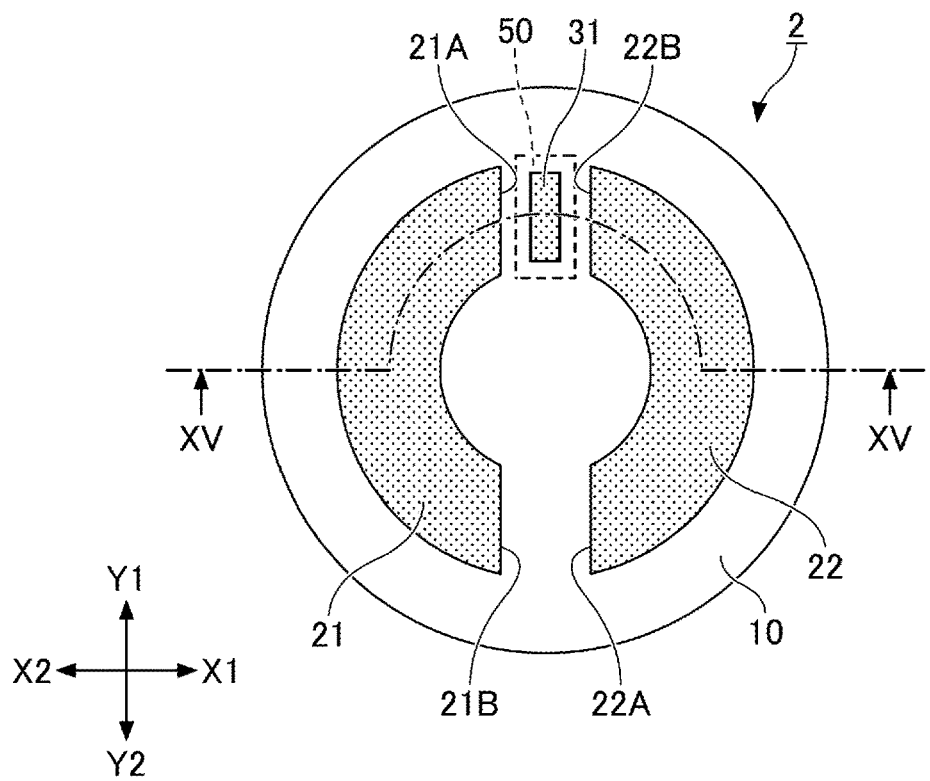
FIG. 14A and FIG. 14B are diagrams illustrating the measuring device according to a second embodiment.
Figure 14B:
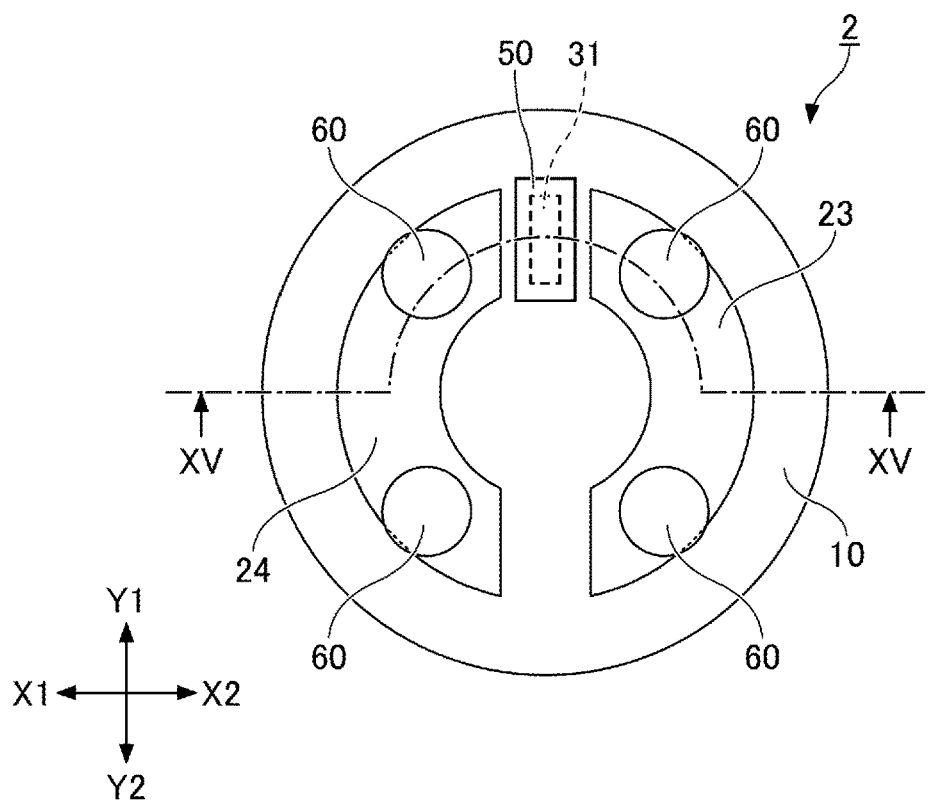
Figure 15:
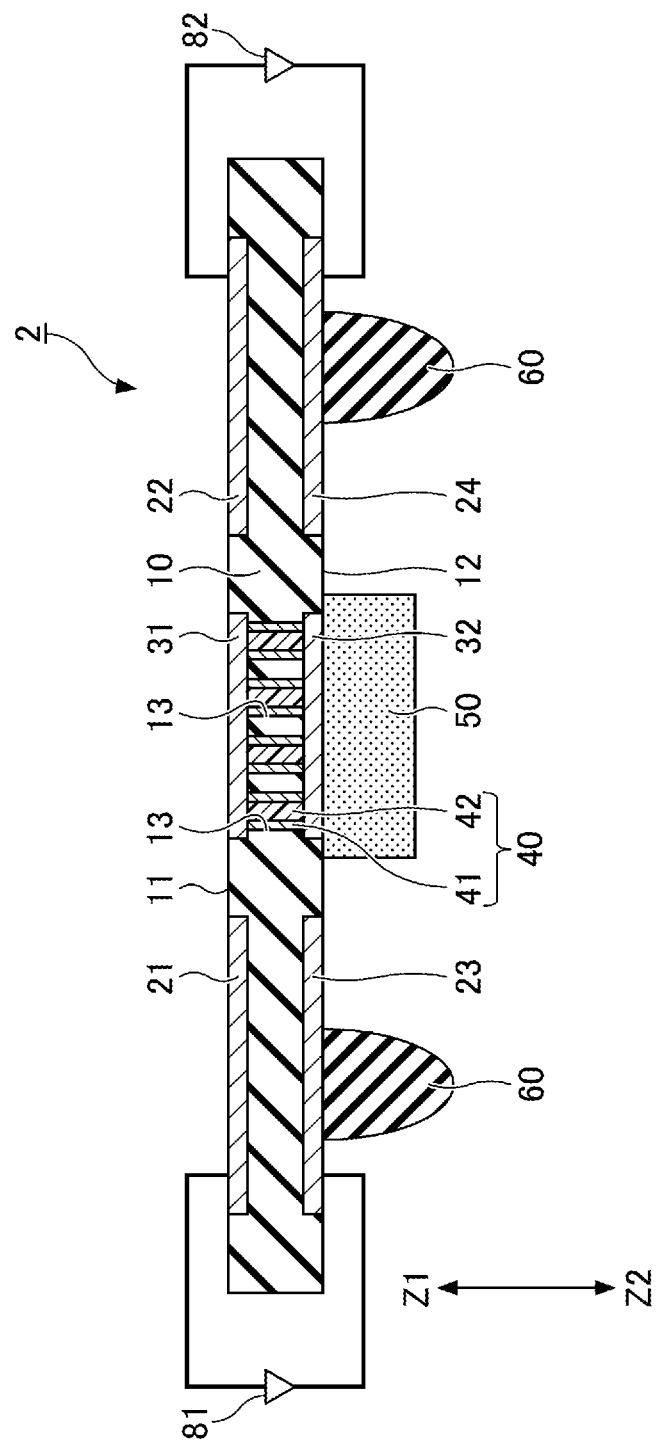
FIG. 15 is a cross sectional view illustrating the measuring device according to the second embodiment.

Next, a second embodiment will be described. The second embodiment relates to the measuring device. FIG. 14A, FIG. 14B, and FIG. 15 are diagrams illustrating the measuring device according to the second embodiment. FIG. 14A is a top view of the measuring device, and FIG. 14B is a bottom view of the measuring device. FIG. 15 corresponds to a cross sectional view along a line XV-XV in FIG. 14A and FIG. 14B.

As illustrated in FIG. 14A, FIG. 14B, and FIG. 15, a measuring device 2 according to the second embodiment includes the substrate 10, the first electrode 21, the second electrode 22, the first copper film 31, the second copper film 32, the heat transfer vias 40, the temperature sensor 50, and the plurality of spacers 60, similar to the measuring device 1. The measuring device 2 further includes a third electrode 23, a fourth electrode 24, a first buffer circuit 81, and a second buffer circuit 82.

The third electrode 23 and the fourth electrode 24 are provided on the second surface 12, for example. The third electrode 23 and the fourth electrode 24 are electrically insulated from each other. Each of the third electrode 23 and the fourth electrode 24 has a planar shape that is approximately arcuate band-shaped, for example. The third electrode 23 and the fourth electrode 24 are curved so as to separate from each other. In the plan view viewed in the direction perpendicular to the first surface 11, the third electrode 23 overlaps the first electrode 21, and the fourth electrode 24 overlaps the second electrode 22. Each of the third electrode 23 and the fourth electrode 24 includes a copper film, for example. Thicknesses of the third electrode 23 and the fourth electrode 24 are in a range of approximately 12 μm to approximately 30 μm, for example.

The first buffer circuit 81 is connected between the first electrode 21 and the third electrode 23. An input of the first buffer circuit 81 is connected to the first electrode 21, and an output of the first buffer circuit 81 is connected to the third electrode 23. The second buffer circuit 82 is connected between the second electrode 22 and the fourth electrode 24. An input of the second buffer circuit 82 is connected to the second electrode 22, and an output of the second buffer circuit 82 is connected to the fourth electrode 24.

Otherwise, the configuration of the measuring device 2 is the same as the configuration of the measuring device 1 according to the first embodiment.

According to the second embodiment, it is also possible to obtain the same effects as those obtainable by the first embodiment. In addition, according to the second embodiment, the third electrode 23 functions as a shield electrode with respect to the first electrode 21, and the fourth electrode 24 functions as a shield electrode with respect to the second electrode 22. For this reason, it is possible to reduce the effects of an electric field from the second surface 12 of the substrate 10, that would otherwise affect the first electrode 21 and the second electrode 22. Hence, it is possible to reduce a noise caused by the electric field from affecting the first electrode 21 and the second electrode 22, and to perform the measurement with an even higher accuracy.

The measuring device 2 according to the second embodiment can also be used in the measuring system, in a manner similar to the measuring device 1.

Reference Example

Figure 16A:
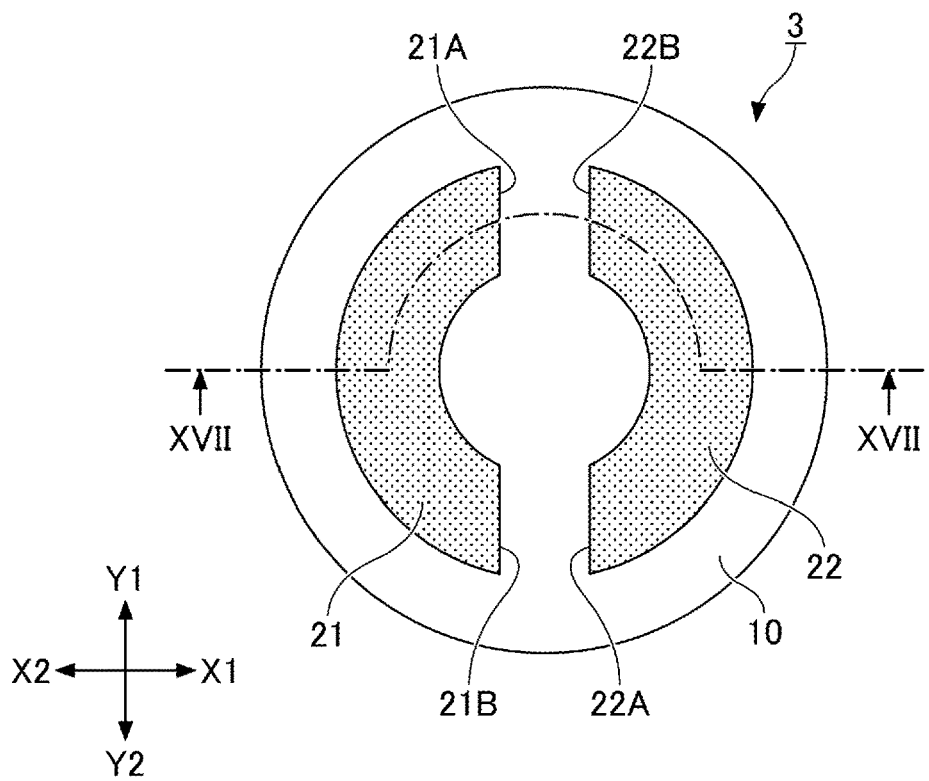
FIG. 16A and FIG. 16B are diagrams illustrating a measuring device according to a reference example.
Figure 16B:
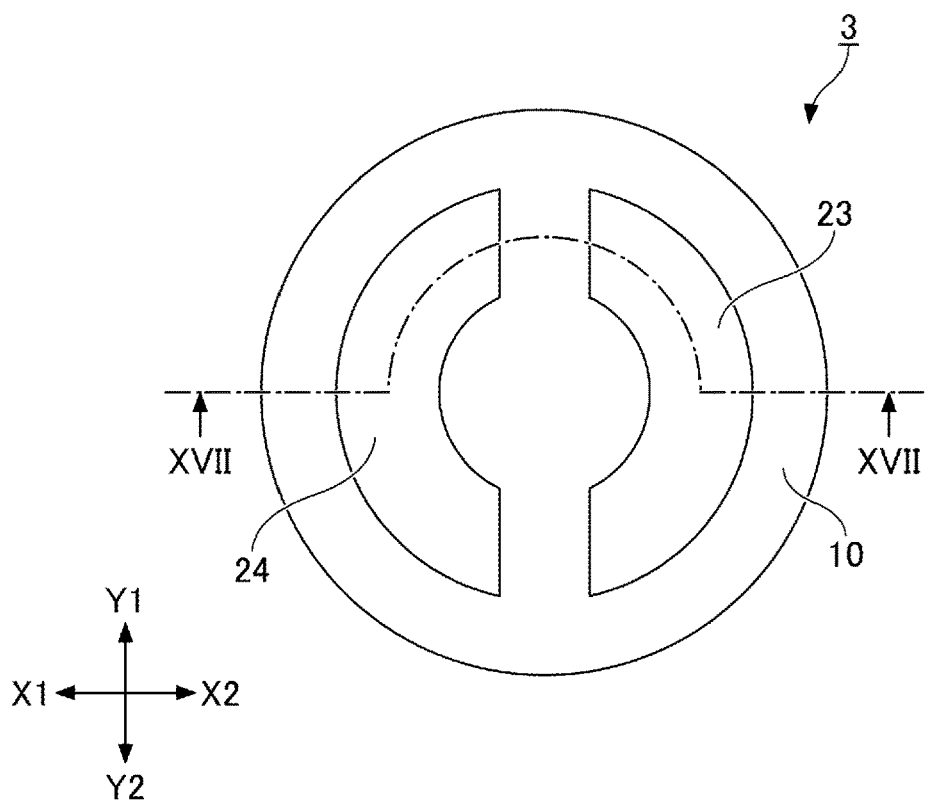
Figure 17:
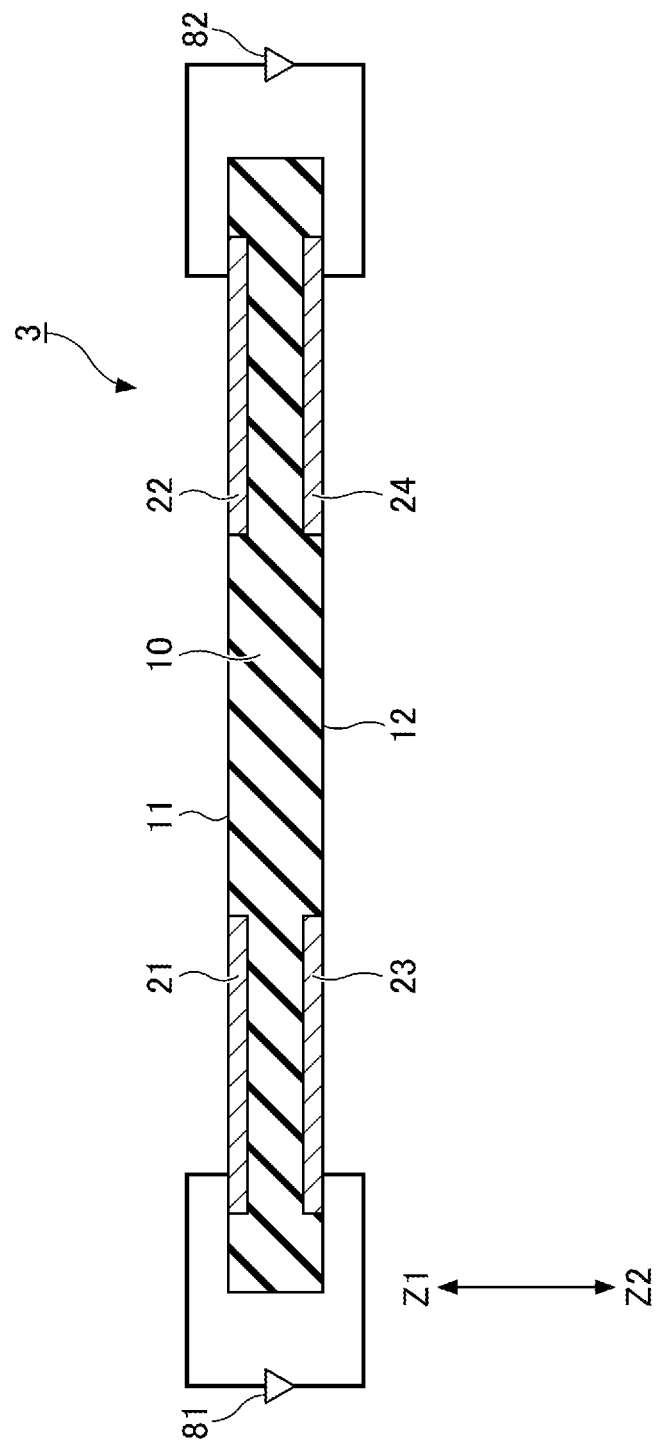
FIG. 17 is a cross sectional view illustrating the measuring device according to the reference example.

Next, a reference example will be described. The reference example relates to a measuring device. FIG. 16A, FIG. 16B, and FIG. 17 are diagrams illustrating the measuring device according to the reference example. FIG. 16A is a top view of the measuring device, and FIG. 16B is a bottom view of the measuring device. FIG. 17 corresponds to a cross sectional view along a line XVII-XVII in FIG. 16A and FIG. 16B.

As illustrated in FIG. 16A, FIG. 16B, and FIG. 17, a measuring device 3 according to the reference example includes the substrate 10, the first electrode 21, the second electrode 22, the third electrode 23, the fourth electrode 24, the first buffer circuit 81, and the second buffer circuit 82, similar to the measuring device 2. However, the measuring device 3 does not include the first copper film 31, the second copper film 32, the heat transfer vias 40, the temperature sensor 50, and the plurality of spacers 60.

Otherwise, the configuration of the measuring device 3 is the same as the configuration of the measuring device 2 according to the second embodiment.

In the measuring device 3 according to the reference example, the third electrode 23 functions as the shield electrode with respect to the first electrode 21, and the fourth electrode 24 functions as the shield electrode with respect to the second electrode 22, similar to the second embodiment. For this reason, it is possible to reduce the effects of an electric field from the second surface 12 of the substrate 10, that would otherwise affect the first electrode 21 and the second electrode 22. Hence, it is possible to reduce a noise caused by the electric field from affecting the first electrode 21 and the second electrode 22, and to perform the measurement with an even higher accuracy.

The measuring device 3 according to the reference example can also be used in the measuring system, in a manner similar to the measuring devices 1 and 2.

In the first embodiment and the second embodiment, it is not necessary to provide a plurality of via holes 13 and a plurality of heat transfer vias 40, and only one via hole 13 may be formed in the substrate 10, and only one heat transfer via 40 may be provided inside the via hole 13.

Further, the physical property to be measured is not limited to the dielectric constant, but may be an electric resistance, for example. Further, the concentration of a substance in a liquid other than water may be measured.

According to the disclosed technique, it is possible to provide a measuring device and a measuring system capable of performing a measurement with a satisfactory measurement accuracy even in the case where physical properties to be measured are temperature dependent.

Although the embodiments are numbered with, for example, "first," or "second," the ordinal numbers do not imply priorities of the embodiments. Many other variations and modifications will be apparent to those skilled in the art.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A measuring device comprising:
   a substrate having a first surface and a second surface on an opposite side from the first surface;
   a first electrode and a second electrode provided on the substrate;
   a heat-sensitive portion, provided on the first surface, and configured to detect heat of a substance that makes contact with the first surface;
   a temperature sensor provided on the second surface; and
   a heat transfer member, penetrating the substrate, and configured to transfer heat of the heat-sensitive portion to the temperature sensor,
   wherein the heat-sensitive portion includes a first copper film.

2. The measuring device as claimed in claim 1, wherein the first electrode and the second electrode are used to detect a dielectric constant between the first electrode and the second electrode.

3. The measuring device as claimed in claim 1, wherein
   the heat-sensitive portion and the temperature sensor overlap each other in a plan view viewed in a direction perpendicular to the first surface, and
   the heat transfer member includes a heat transfer via extending in the direction perpendicular to the first surface.

4. The measuring device as claimed in claim 3, wherein
   the heat transfer member includes a second copper film provided on the second surface and making contact with the heat transfer via, and
   the temperature sensor makes contact with the second copper film.

5. The measuring device as claimed in claim 1, wherein the heat transfer member includes a second copper film making contact with the heat-sensitive portion.

6. The measuring device as claimed in claim 1, further comprising:
   a third electrode and a fourth electrode provided on the second surface;
   a first buffer circuit electrically connected between the first electrode and the third electrode; and
   a second buffer circuit electrically connected between the second electrode and the fourth electrode,
   wherein the first electrode and the third electrode overlap each other, and the second electrode and the fourth electrode overlap each other, in a plan view viewed in a direction perpendicular to the first surface.

7. The measuring device as claimed in claim 1, wherein each of the first electrode and the second electrode has a planar shape that is approximately arcuate band-shaped.

8. The measuring device as claimed in claim 1, wherein the first electrode and the second electrode are electrically insulated from each other.

9. The measuring device as claimed in claim 1, further comprising:
   a plurality of spacers provided on the second surface,
   wherein each of the plurality of spacers has a thickness greater than a thickness of the temperature sensor.

10. The measuring device as claimed in claim 3, wherein the heat transfer via includes
    a via hole penetrating the substrate,
    a second copper film covering an inner wall surface of the via hole, and a filler material filling an inner side of the second copper film.

11. A measuring system comprising:
a measuring device including:
  a substrate having a first surface and a second surface on an opposite side from the first surface,
  a first electrode and a second electrode provided on the substrate,
  a heat-sensitive portion, provided on the first surface, and configured to detect heat of a substance that makes contact with the first surface,
  a temperature sensor provided on the second surface, and
  a heat transfer member, penetrating the substrate, and configured to transfer heat of the heat-sensitive portion to the temperature sensor;
a detection circuit configured to detect a dielectric constant between the first electrode and the second electrode; and
a processor configured to compute a physical property of a measuring object placed on the first surface, from an output signal of the temperature sensor and an output signal of the detection circuit.

12. The measuring system as claimed in claim 11, wherein the measuring object includes a container, and water sealed inside the container.

13. The measuring system as claimed in claim 11, wherein the heat-sensitive portion of the measuring device includes a copper film.

* * * * *